United States Patent
Beutel et al.

(10) Patent No.: US 12,059,234 B2
(45) Date of Patent: Aug. 13, 2024

(54) METHOD AND A SYSTEM FOR ESTIMATING A MEASURE OF CARDIOVASCULAR HEALTH OF A SUBJECT

(71) Applicant: Stichting IMEC Nederland, AE Eindhoven (NL)

(72) Inventors: Fabian Beutel, Duesseldorf (DE); Evelien Hermeling, Soerendonk (NL)

(73) Assignee: STICHTING IMEC NEDERLAND, Eindhoven (NL)

( * ) Notice: Subject to any disclaimer, the term of this patent is extended or adjusted under 35 U.S.C. 154(b) by 98 days.

(21) Appl. No.: 17/368,648

(22) Filed: Jul. 6, 2021

(65) Prior Publication Data
US 2022/0000378 A1    Jan. 6, 2022

(30) Foreign Application Priority Data
Jul. 6, 2020 (EP) .................................... 20184209

(51) Int. Cl.
*A61B 5/021* (2006.01)
*A61B 5/0285* (2006.01)
(Continued)

(52) U.S. Cl.
CPC ........ *A61B 5/02125* (2013.01); *A61B 5/0285* (2013.01); *A61B 5/352* (2021.01);
(Continued)

(58) Field of Classification Search
CPC ... A61B 5/02125; A61B 5/0285; A61B 5/352; A61B 8/02; A61B 8/04; A61B 8/06;
(Continued)

(56) References Cited

U.S. PATENT DOCUMENTS

| 2013/0041268 A1* | 2/2013 | Rimoldi ................. | A61B 5/349 600/479 |
| 2017/0055853 A1* | 3/2017 | Kirenko ............. | A61B 5/02125 |
| 2020/0229718 A1* | 7/2020 | Spencer ............ | A61B 5/02125 |

FOREIGN PATENT DOCUMENTS

| DE | 202016105262 U1 | 12/2016 |
| WO | WO-2007023426 A2 | 3/2007 |
| WO | WO-2015118544 A1 | 8/2015 |

OTHER PUBLICATIONS

Van Houwelingen et al., The Onset of Ventricular Isovolumic Contraction as Reflected in the Carotid Artery Distension Waveform, Ultrasound in Medicine and Biology, New York, NY, US, vol. 33, No. 3, Mar. 1, 2007 (Mar. 1, 2007), pp. 371-378, XP022110714, ISSN: 0301-5629. (Year: 2007).*

(Continued)

*Primary Examiner* — Alexei Bykhovski
(74) *Attorney, Agent, or Firm* — MOSER TABOADA

(57) ABSTRACT

A method for estimating a measure of cardiovascular health of a subject (102) comprises: receiving (302) an electrocardiogram, ECG, signal (202); receiving (304) an artery signal (210) representative of pressure pulse wave propagation at a location in an artery; determining (306) a fiducial point in time based on the ECG signal (202) providing an indication of onset of isovolumetric contraction; determining (308) a pre-systolic pressure pulse arrival point in time (212) based on the artery signal (210) to correspond to the onset of the isovolumetric contraction being reflected in the artery signal (210), determining (310) a time period between the onset of the isovolumetric contraction and the pre-systolic pressure pulse arrival point in time, said time period representing a vascular transit time; and determining (312) a pulse wave velocity of the subject (102) based on a physical distance between an aortic valve and the location in the artery and on the vascular transit time.

11 Claims, 6 Drawing Sheets

(51) Int. Cl.
- *A61B 5/352* (2021.01)
- *A61B 8/02* (2006.01)
- *A61B 8/04* (2006.01)
- *A61B 8/06* (2006.01)
- *A61B 8/08* (2006.01)
- *G16H 10/60* (2018.01)
- *G16H 40/67* (2018.01)
- *G16H 50/30* (2018.01)
- *G16H 50/70* (2018.01)

(52) U.S. Cl.
CPC .......... *A61B 8/02* (2013.01); *A61B 8/04* (2013.01); *A61B 8/06* (2013.01); *A61B 8/5223* (2013.01); *G16H 10/60* (2018.01); *G16H 40/67* (2018.01); *G16H 50/30* (2018.01); *G16H 50/70* (2018.01)

(58) Field of Classification Search
CPC .......... A61B 8/5223; A61B 2562/0219; A61B 5/02416; A61B 8/4236; G16H 10/60; G16H 40/67; G16H 50/30; G16H 50/70
See application file for complete search history.

(56) References Cited

OTHER PUBLICATIONS

Van Houwelingen et al., "The Onset of Ventricular Isovolumic Contraction as Reflected in the Carotid Artery Distension Waveform", Ultrasound in Medicine and Biology, New York, NY, US, vol. 33, No. 3, Mar. 1, 2007 (Mar. 1, 2007), pp. 371-378, XP022110714, ISSN: 0301-5629.

E. Hermeling: "Local pulse wave velocity determination: the arterial distension waveform from foot to crest", Jan. 1, 2009 (Jan. 1, 2009), XP055699249, Retrieved from the Internet: URL: https://oris.maastrichtuniversity.nl/ws/portalfiles/portal/798251/guld-81854c25-e70a-499e-9392-9be43dbt473a-ASSET1.0.pdf [retrived on May 28, 2020].

Fletcher, Richard Ribon, and Sarang Kulkarni. "Wearable Doppler Radar with Integrated Antenna for Patient Vital Sign Monitoring." IEEE, 2010. 276-279. Web. © 2010 IEEE.

Solberg et al., "Experimental investigation into radar-based central blood pressure estimation", IET Radar Sonar Navig., pp. 1-9 © The Institution of Engineering and Technology (2014), doi: 10.1049/iet-rsn.2014.0206.

Dilpreet et al., "A survey on signals and systems in ambulatory blood pressure monitoring using pulse transit time", Physiol. Meas. 36 (2015) R1-R26, doi:10.1088/0967-3334/36/3/R1.

European Search Report dated Nov. 5, 2020 for application No. EP20184209.

* cited by examiner

METHOD AND A SYSTEM FOR ESTIMATING A MEASURE OF CARDIOVASCULAR HEALTH OF A SUBJECT

CROSS-REFERENCE TO RELATED APPLICATIONS

The current application is national phase of European Application No. 20184209.3, filed Jul. 6, 2020, which patent documents are incorporated herein in their entireties.

TECHNICAL FIELD

The present inventive concept relates to estimating a measure of cardiovascular health of a subject.

BACKGROUND

Cardiovascular disease is a common problem. It is therefore of large interest to enable estimating cardiovascular health of subjects in a simple and robust manner.

Pulse wave velocity (PWV) is a measure of interest, which may provide a clinical measure of arterial stiffness and which may also be used for estimating blood pressure of a subject.

At present, a clinical gold standard measure is carotid-to-femoral PWV ($PWV_{cf}$), which may be estimated from a distance between two anatomic landmarks divided by a differential time interval measurement. The use of two different anatomic landmarks enables an influence of cardiac isovolumetric contraction (IVC) on determination of the time for a pulse to travel from the aortic valve to the respective landmark to be canceled out. This is because the IVC delay adds to both time durations for a pulse to travel from the aortic valve to the respective landmark. Hence, when subtracting one time duration from the other, the IVC delay will cancel out.

However, measurements at plural anatomic landmarks may require a fairly complicated system with plural sensors and the use of such a system still requires specially trained operators.

It would therefore be desired to have a simple system which enables robust determination of PWV.

In M. J. van Houwelingen, P. J. Barenbrug, M. C. Hoeberigs, R. S. Reneman, and A. P. G. Hoeks, "The onset of ventricular isovolumic contraction as reflected in the carotid artery distension waveform," *Ultrasound Med. Biol.*, vol. 33, no. 3, pp. 371-378, 2007, it is indicated that an isovolumetric ventricular contraction may be determined from a distension waveform of blood pressure propagation at an a peripheral location. Also, it is indicated that correction for pre-ejection period may be needed for correct estimation of PWV. No indication of determination of PWV is however provided, so there is still a need of enabling an improved determination of the PWV.

SUMMARY

An objective of the present inventive concept is to provide robust estimation of a measure of cardiovascular health of a subject using a compact system. It is a particular object to enable estimation using a sensor for detecting pressure pulse wave propagation at a single location in an artery of the subject.

These and other objectives of the present inventive concept are at least partly met by the invention as defined in the independent claims. Preferred embodiments are set out in the dependent claims.

According to a first aspect, there is provided a method for estimating a measure of cardiovascular health of a subject, said method comprising: receiving an electrocardiogram, ECG, signal of the subject; receiving an artery signal representative of pressure pulse wave propagation at a location in an artery of the subject; determining a fiducial point in time based on the ECG signal, said fiducial point in time providing an indication of onset of isovolumetric contraction of the subject's heart; determining a pre-systolic pressure pulse arrival point in time based on the artery signal, wherein the pre-systolic pressure pulse arrival point in time is determined to correspond to the onset of the isovolumetric contraction of the subject's heart being reflected in the artery signal, determining a time period between the onset of the isovolumetric contraction of the subject's heart and reflection of the onset of the isovolumetric contraction of the subject's heart in the artery signal based on the fiducial point in time and the pre-systolic pressure pulse arrival point in time, said time period representing a vascular transit time; and determining a pulse wave velocity of the subject based on a physical distance between an aortic valve and the location in the artery and on the vascular transit time.

Thanks to the present inventive concept, it is possible to determine a pulse wave velocity of the subject. The pulse wave velocity may be accurately determined based on receiving an artery signal representative of pressure pulse wave propagation at a location in an artery of the subject. This artery signal in combination with an ECG signal may be used for determining the pulse wave velocity and it is not necessary to acquire further measurements in order to avoid influence of isovolumetric contraction of the subject's heart on the determined pulse wave velocity.

In particular, there is a pre-ejection period (PEP) in the cardiac function which represents a time elapsed between electrical depolarization of the left ventricle (as represented by QRS features of the ECG signal) and beginning of ventricular ejection, i.e. blood being ejected from the left ventricle into the aorta. When estimating a time duration for a pressure pulse to propagate from the aortic valve to a location in an artery using the ECG signal, the PEP may add to the time duration such that an incorrect duration of the actual pressure pulse propagation is determined. The PEP is defined by a sum of an electromechanical delay (EMD) and an isovolumetric contraction (IVC) of the left ventricle. The EMD may be assumed to be constant (approximately 40 ms) and may therefore easily be compensated for, whereas the IVC may differ between different subjects.

It is an insight of the present inventive concept, that influence of the IVC on the pulse wave velocity may be avoided by determining a fiducial point representing a point in time based on the ECG signal that gives an indication for determining an onset of the isovolumetric contraction of the subject's heart and determining a pre-systolic pressure pulse arrival point in time representing a point in time based on the artery signal that provides a corresponding time point in the cardiac cycle. Thus, it is an insight of the present inventive concept, that the time period between the onset of the isovolumetric contraction as indicated by the fiducial point and the pre-systolic pressure pulse arrival point may include only a duration corresponding to the duration of a pressure pulse wave propagating from the aortic valve to the location at the artery. This time period may thus be directly used in determining a pulse wave velocity (PVVV) avoiding influence of the IVC.

It may be relatively simple to determine the fiducial point providing an indication of onset of the isovolumetric contraction of the subject's heart based on the ECG signal, since this fiducial point may be determined based on detection of a feature in the QRS complex, e.g. an R-peak. It may further be relatively simple to determine arrival time of a pressure pulse wave in the artery signal. However, a time duration between such points in time would include the IVC duration and thus not correctly represent the time elapsed for the pressure pulse wave to propagate from the aortic valve to the location at the artery. While an end point of the IVC may not easily be detected in the ECG signal, it has been realized that it is possible to detect a pre-systolic pressure pulse arrival point in time in the artery signal that precedes arrival of the pressure pulse wave by a duration corresponding to the IVC duration.

Thus, it is an insight of the present inventive concept, which has further been proven by experiments described in the detailed description, that it is possible to determine a pre-systolic pressure pulse arrival point in time in the artery signal such that a time period representing a vascular transit time may be determined based on the pre-systolic pressure pulse arrival point in time and the fiducial point providing an indication of onset of isovolumetric contraction of the subject's heart without a need to make any further measurements and/or analysis of time points in the ECG signal and/or the artery signal.

The method for estimating a measure of cardiovascular health may be implemented in a simple, compact system. There is only a need of a single sensor to detect an artery signal at a single location in order to enable determination of a PWV. In comparison, determination of carotid-to-femoral PWV ($PWV_{cf}$) requires two sensors arranged at the carotid artery and the femoral artery. However, it should be realized that according to the present inventive concept more than one artery signal may still be acquired, which could be used e.g. for determining a PWV of a central artery and a PWV of a peripheral artery or for determining different PWVs along an artery.

The method may use a single sensor for detecting an artery signal in combination with an ECG sensor, which makes the method suitable for continuous monitoring of the cardiovascular health of the subject as the sensors may be worn without largely affecting daily life of a wearer.

The PWV is a useful measure which can e.g. be used as input for determining arterial stiffness of a subject. Hence, the PWV may provide input for directly estimating cardiovascular health of the subject. Further, PWV may also be used as input for estimating other measures of cardiovascular health. For instance, PWV may be used for estimating blood pressure of a subject.

As an alternative, it may be possible to estimate blood pressure of a subject from determination of the vascular transit time, while not necessarily determining the PWV. Hence, according to an embodiment, the method may comprise using the vascular transit time to determine a measure of cardiovascular health of the subject, wherein such measure may be e.g. the PWV or a blood pressure. At least, the vascular transit time may be used to follow relative changes in blood pressure.

As used herein, the term "artery signal" should be construed as any signal representative of pressure pulse wave propagating in an artery. The artery signal may thus be acquired in many different manners, using a non-invasive sensor arranged outside a body of the subject, such as arranged on the skin of the subject in relation to the location in the artery. For example, the artery signal may be acquired by passive sensing, such as acquiring vibrations caused by pressure pulse wave propagation or by active sensing, such as transmitting a signal to the artery and detecting a response to the transmitted signal for detecting pressure pulse wave propagation.

The ECG signal and the artery signal may be received as digital signals. Thus, a signal may be acquired by an ECG sensor and be subject to analog-to-digital conversion to form a digital ECG signal. Similarly, a signal may be acquired by s sensor and be subject to analog-to-digital conversion to form a digital artery signal. Thus, the method may receive digital signals forming the ECG signal and the artery signal. This implies that processing of the ECG signal and the artery signal may be performed in digital domain.

As used herein, the term "fiducial point in time" represents a point in time providing an indication of onset of isovolumetric contraction of the subject's heart. It should be realized that the fiducial point in time determined based on the ECG signal need not necessarily correspond to the onset of the isovolumetric contraction of the subject's heart. Rather, the fiducial point in time that may easily be detected from the ECG signal may have a known relation to the onset of the isovolumetric contraction of the subject's heart, such that the onset of the isovolumetric contraction may be determined based on the fiducial point in time.

Further, as used herein, the phrase "pre-systolic pressure pulse arrival point in time is determined to correspond to the onset of the isovolumetric contraction of the subject's heart being reflected in the artery signal" implies that the pre-systolic pressure pulse arrival point in time is a point in time in the artery signal that relates to the arrival of the pressure pulse wave in a corresponding manner as the onset of the isovolumetric contraction of the subject's heart relates to onset of blood being ejected out of the left ventricle. The artery signal might not comprise a feature that can intuitively be explained to reflect or represent onset of the isovolumetric contraction of the subject's heart. However, it is an insight of the invention, that it is possible to accurately determine a pre-systolic pressure pulse arrival point in time in the artery signal, wherein the pre-systolic pressure pulse arrival point in time precedes the arrival of the pressure pulse wave by a duration corresponding to the IVO duration.

According to an embodiment, determining the pre-systolic pressure pulse arrival point in time comprises determining a second derivative of the artery signal and determining a local maximum in the second derivative.

It has been found that a local maximum in the second derivative is a clear determinant of the pre-systolic pressure pulse arrival point in time of the artery signal. Thus, determining the pre-systolic pressure pulse arrival point in time using the second derivative provides a robust manner of correctly determining the pre-systolic pressure pulse arrival point in time.

However, it should be realized that it may be possible to determine the pre-systolic pressure pulse arrival point in time in other manners as well. For instance, the pre-systolic pressure pulse arrival point in time may be determined based on analysis of the artery signal, a first derivative of the artery signal, a third derivative of the artery signal, fitting a Gaussian curve to the second derivative of the artery signal.

According to an embodiment, the artery signal is received from an ultrasound sensor.

An ultrasound sensor may be used for detecting the artery signal as a response to an ultrasound signal transmitted towards the artery. An artery signal obtained by an ultrasound sensor may clearly represent the pressure pulse wave propagation in the artery to allow robust detection of arrival of the pressure pulse wave at the artery.

The ultrasound sensor may be compact and arranged on a small carrier, such as a patch, that may be locally arranged in relation to a location of the artery of interest.

The ultrasound sensor may further be configured to be arranged in contact with skin of the subject. The ultrasound sensor may thus be placed in contact with the skin, without a need to pinch or clamp the skin of the subject for improving the relation between the sensor and the artery (as may be needed when using a tonometer that may need direct mechanical coupling with the artery).

This ensures that the ultrasound sensor may be comfortably worn so as to facilitate continuous monitoring by the subject wearing the ultrasound sensor for a long period of time.

According to an embodiment, the received artery signal comprises an ultrasound-based distension waveform.

Hence, the artery signal may represent changes to a diameter of the artery as caused by pressure pulse wave and blood flow propagating through the artery. The distension waveform may be suitable for robustly determining the pre-systolic pressure pulse arrival point in time in the artery signal.

According to an embodiment, the method further comprises acquiring the artery signal by a sensor. The artery signal may in some embodiments be acquired by an ultrasound sensor. In some embodiments, the method comprises acquiring a distension waveform by an ultrasound sensor.

According to an embodiment, the artery signal is received from an optical sensor, a piezoelectric tonometer, a bio-impedance sensor or a radio frequency sensor.

Thus, the artery signal need not necessarily be received from an ultrasound sensor, but other alternatives may be considered. For instance, a sensor based on optical principles, such as a photoplethysmography sensor or an optical coherence tomography sensor may be used. The sensor may be used for detecting an artery signal representing pressure pulse wave and/or blood flow propagating through the artery.

It should further be realized that the artery signal may be a waveform that represents pressure pulse wave and/or blood flow propagating through the artery in one of several different ways. For instance, the artery signal may be a distension waveform that represents changes to the diameter of the artery, but the artery signal may e.g. alternatively be a pressure waveform that represents changes of pressure in the artery.

According to an embodiment, the received artery signal is representative of pressure pulse wave propagation at a location in a carotid artery.

It may be possible to obtain a strong signal of pressure pulse wave propagation in the carotid artery such that using an artery signal from a carotid artery allows accurate determination of the PWV.

Further, using the carotid artery enables determination of a central PWV, i.e. a PWV through large arteries.

According to an embodiment, the method further comprises estimating blood pressure of the subject based on the determined pulse wave velocity.

Blood pressure is a measure that is of high interest for generally assessing cardiovascular health of the subject. However, blood pressure is normally acquired using an inflatable cuff, which is inconvenient, and may require a trained operator for correctly determining the blood pressure. Also, the blood pressure may be affected by circumstances in which it is acquired, e.g. in a doctor's office, such that the acquired blood pressure does not accurately reflect the subject's health. A correct estimation of PWV may be used for determining a corresponding blood pressure. Hence, the method estimating blood pressure based on determined PWV may advantageously provide an estimate of blood pressure using a system that may be worn for a long time and which may imply that the blood pressure is not increased by the circumstances in which it is measured.

Further, the PWV may be determined for each cardiac cycle as the artery signal may be compared to ECG signal in each cardiac cycle. This also implies that blood pressure may be estimated each cardiac cycle such that changes in PWV and blood pressure may be detected very quickly.

According to an embodiment, determining the fiducial point in time comprises determining an R peak in the ECG signal.

The R peak may be easy to detect in the ECG signal and may therefore suitably be used in determining the fiducial point in time in the ECG signal.

According to an embodiment, the onset of the isovolumetric contraction of the subject's heart is offset from the fiducial point in time by a half of an electromechanical delay period.

The R peak does not represent the onset of the isovolumetric contraction of the subject's heart. However, the R peak may relate to the onset of the isovolumetric contraction of the subject's heart by an offset that is constant at least for an individual subject.

The electromechanical delay period may be assumed to be constant and have a duration of 40 ms. Further, half of the electromechanical delay period may be assumed to elapse between a Q point in the ECG signal and the R peak, such that the R peak would precede the onset of the isovolumetric contraction by half of the electromechanical delay period and thus normally by 20 ms. This constant offset value of 20 ms may thus be used for determining the fiducial point in time.

In order to increase accuracy for an individual subject, the electromechanical delay period may be determined accurately once for the subject. For instance, for particular subjects, such as subjects with a certain heart disease or having prior damage to myocardium, the electromechanical delay period may not correspond to normal values. Then, an individually determined value for the electromechanical delay period may be used for determining the relation between the fiducial point in time and onset of the isovolumetric contraction.

According to another embodiment, determining the fiducial point in time comprises determining a Q point in the ECG signal.

Thus, the R peak of the ECG signal need not necessarily be used for determining the fiducial point in time. According to one alternative, the Q point may be used. However, it should be realized that other features of the ECG signal may also or alternatively be used. Depending on the feature of the ECG signal being used, a different offset from the fiducial point in time will preside and the determining the onset of isovolumetric contraction of the subject's heart may use a corresponding offset for compensating for the difference between the onset of isovolumetric contraction and the feature extracted from the ECG signal.

As used herein, the term "Q point" should be understood as a local minimum of the ECG signal preceding the R peak. The ECG signal may some times be described as comprising a Q wave, and the local minimum may be referred to as the Q wave and, when referring to the local minimum the terms "Q point" and "Q wave" may be used interchangeably.

According to an embodiment, said artery signal is a first artery signal representative of pressure pulse wave propagation at a first location in a first artery of the subject, said pre-systolic pressure pulse arrival point in time is a first pre-systolic pressure pulse arrival point in time, said time period is a first time period, said vascular transit time is a first vascular transit time, and said pulse wave velocity is a first pulse wave velocity, wherein the method further comprises: receiving a second artery signal representative of pressure pulse wave propagation at a second location in the first artery of the subject or in a second artery of the subject; determining a second pre-systolic pressure pulse arrival point in time based on the second artery signal, wherein the second pre-systolic pressure pulse arrival point in time is determined to correspond to the onset of the isovolumetric contraction of the subject's heart being reflected in the second artery signal, determining a second time period between the onset of the isovolumetric contraction of the subject's heart and reflection of the onset of the isovolumetric contraction of the subject's heart in the second artery signal based on the fiducial point in time and the second pre-systolic pressure pulse arrival point in time, said second time period representing a second vascular transit time; and determining a second pulse wave velocity of the subject based on a physical distance between the aortic valve and the second location and on the second vascular transit time.

Thus, by receiving a second artery signal, a second PWV may be determined. For instance, a first PWV representing a pulse wave propagation in central arteries may be determined and a second PWV representing pulse wave propagation in peripheral arteries may be determined. Thus, the first and second PWV may be used in combination for providing information of cardiovascular health of the subject.

As mentioned above, each of the first artery signal and the second artery signal may be processed individually in order to determine a first and a second PWV, respectively. However, additionally or as an alternative, feature(s) of the first artery signal may be compared to feature(s) of the second artery signal. For instance, the first pre-systolic pressure pulse arrival point in time may be compared to the second pre-systolic pressure pulse arrival point in time and/or an arrival time of a pressure pulse wave in the first artery signal may be compared to an arrival time of a pressure pulse wave in the second artery signal. This may be used for determining a PWV between the first location and the second location. Since features of the artery signals are compared, any influence of the IVO on the determined PWV may be avoided.

Further, the IVO duration is the same regardless whether analysis of the first artery signal or the second artery signal is performed. Thus, the IVO duration may be determined based on one of the first and the second artery signal, as a duration between the pre-systolic pressure pulse arrival point in time and an arrival time of the pressure pulse wave. For the other of the first and the second artery signal, the determined IVO duration may be used and subtracted from a time period determined between the onset of the isovolumetric contraction and the arrival time of the pressure pulse wave in the artery signal. Thus, the pre-systolic pressure pulse arrival point in time need not be determined for the second artery signal to determine a correspondence to the onset of the isovolumetric contraction of the subject's heart being reflected in the artery signal. For instance, when the artery signal is received from a peripheral location, the features of the artery signal may not be as strongly emphasized as for an artery signal from a central location and therefore the determining of the pre-systolic pressure pulse arrival point in time may not be as accurately made in such artery signal and using the arrival time of the pressure pulse wave may improve accuracy of determining the second PWV.

According to a second aspect, there is provided a computer program product comprising computer-readable instructions such that when executed on a processing unit the computer-readable instructions will cause the processing unit to perform the method according to the first aspect.

Effects and features of this second aspect are largely analogous to those described above in connection with the first aspect. Embodiments mentioned in relation to the first aspect are largely compatible with the second aspect.

The computer program product may implement the method in a processing unit, which may be a dedicated processing unit for performing the method or may be a general-purpose processing unit which may be able to perform the method based on the computer program product.

The computer program product may be provided on a computer-readable medium provided with the computer-readable instructions, such as any computer-readable medium on which the computer-readable instructions may be stored. However, the computer program product may also or alternatively be downloaded from a server, such that the computer program product may be provided as a signal carrying the computer-readable instructions being downloaded.

According to a third aspect, there is provided a system for estimating a measure of cardiovascular health of a subject, said system comprising: an electrocardiogram, ECG, sensor configured to acquire an ECG signal of the subject; an artery signal sensor configured to acquire an artery signal representative of pressure pulse wave propagation at a location in an artery of the subject; and a processing unit configured to: receive the ECG signal and the artery signal; determine a fiducial point in time based on the ECG signal, said fiducial point in time providing an indication of onset of isovolumetric contraction of the subject's heart; determine a pre-systolic pressure pulse arrival point in time based on the artery signal, wherein the pre-systolic pressure pulse arrival point in time is determined to correspond to the onset of the isovolumetric contraction of the subject's heart being reflected in the artery signal, determine a time period between the onset of the isovolumetric contraction of the subject's heart and reflection of the onset of the isovolumetric contraction of the subject's heart in the artery signal based on the fiducial point in time and the pre-systolic pressure pulse arrival point in time, said time period representing a vascular transit time; and determine a pulse wave velocity of the subject based on a physical distance between an aortic valve and the location in the artery and on the vascular transit time.

Effects and features of this third aspect are largely analogous to those described above in connection with the first and second aspects. Embodiments mentioned in relation to the first and second aspects are largely compatible with the third aspect.

The system may enable determining of the PWV using wearable device(s) that may be worn by the subject for a prolonged period of time to estimate the PWV while minimally affecting daily life of the subject.

The ECG sensor and the artery signal sensor may be arranged in physically separate units, which may each be worn by the subject. However, the ECG sensor and the artery signal sensor may alternatively be commonly arranged in relation to the subject, e.g. by being arranged in a common garment worn by the subject.

The ECG sensor may be configured to perform analog-to-digital conversion to form a digital ECG signal. Similarly, the artery signal sensor may be configured to perform analog-to-digital conversion to form a digital artery signal. Alternatively, analog-to-digital conversion may be performed in an intermediate unit. Thus, the processing unit may be configured to receive digital signals forming the ECG signal and the artery signal. This implies that processing of the ECG signal and the artery signal may be performed in digital domain.

The ECG sensor and the artery signal sensor may communicate with each other e.g. through wired or wireless communication. The processing unit may be arranged integrated with one of the ECG sensor and the artery signal sensor such that communication between the ECG sensor and the artery signal sensor may ensure that the processing unit receives the ECG signal and the artery signal for processing the signals and determining the PWV of the subject.

The processing unit may alternatively be arranged in a separate housing, which may or may not be worn by the subject. The ECG sensor and the artery signal sensor may communicate for packaging the ECG signal with the artery signal such that both signals may be further communicated to the processing unit from either the ECG sensor or the artery signal sensor. Alternatively, the processing unit may receive the ECG signal and the artery signal by communicating with each of the ECG sensor and the artery signal sensor.

The processing unit being provided in a wearable device may provide that the subject may be presented with the measure of the cardiovascular health in the wearable device in real time. Thus, the subject may continuously check information of the cardiovascular health. The processing unit may be arranged in a device that the subject may anyway wear, such as in a smartwatch.

Alternatively, the processing unit may be provided in a unit that may not necessarily be worn by the subject, but which may be available for short-range communication with the ECG sensor and the artery signal sensor, such as the processing unit being arranged in a smartphone.

As a further alternative, the processing unit may be provided anywhere, such as "in the cloud". The processing unit may communicate with the ECG sensor and the artery signal sensor through a computer network, such as the Internet, enabling the processing unit to be arranged anywhere in relation to the ECG sensor and the artery signal sensor. The processing unit may communicate results of the determination of the PWV of the subject back to the subject to enable presentation to the subject, e.g. communicating to a smartphone, to a wearable device, or to the ECG sensor or the artery signal sensor.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
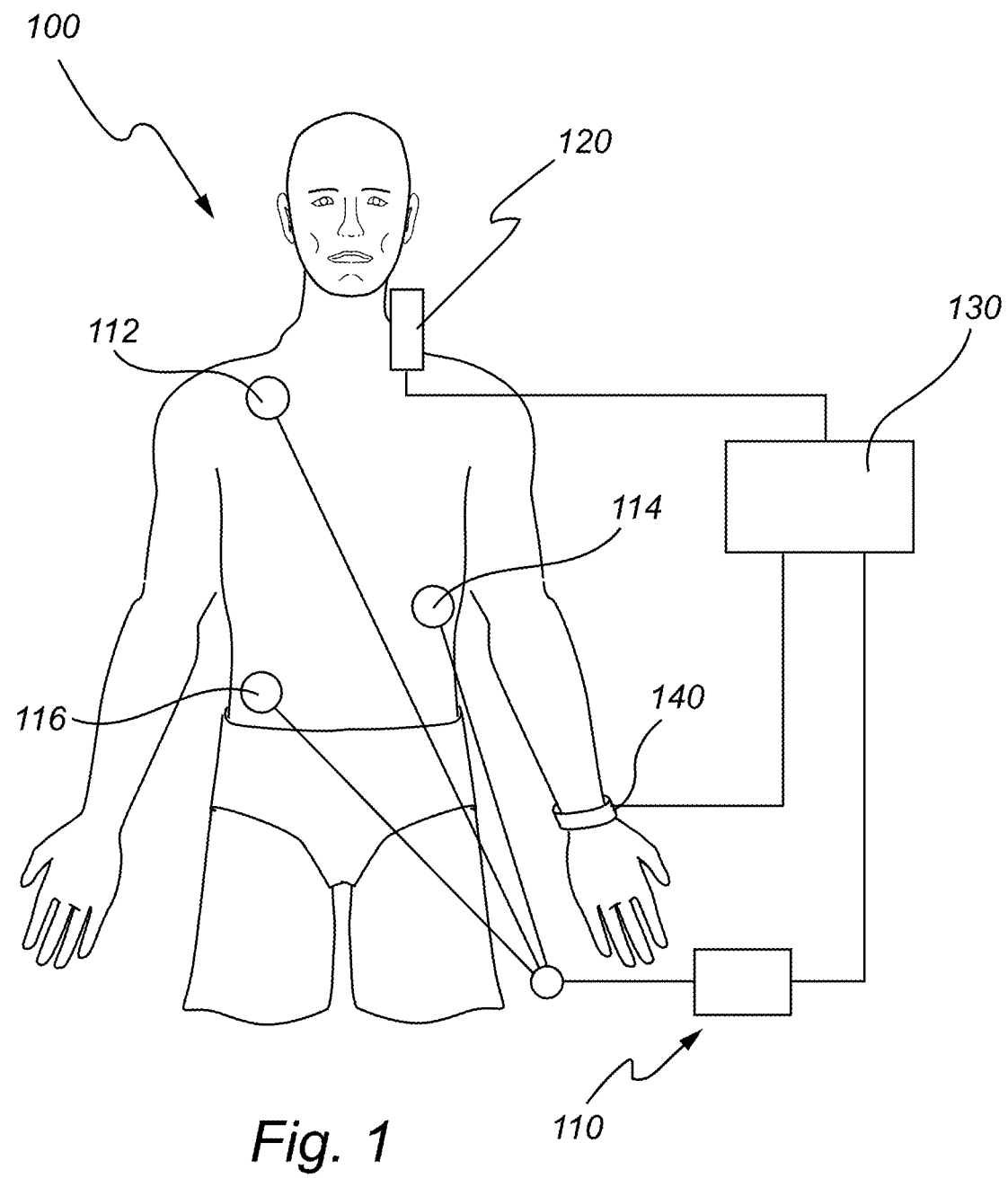
FIG. 1 is a schematic view of a system according to an embodiment.

Referring now to FIG. 1, a system 100 for estimating a measure of cardiovascular health of a subject 102 is described.

The system 100 may comprise an electrocardiogram (ECG) sensor 110 configured to acquire an ECG signal of the subject 102. As shown in FIG. 1, the ECG sensor 110 may comprise a plurality of electrodes 112, 114, 116, which may be commonly connected to a signal acquisition unit 118 for acquiring the ECG signal.

The electrodes 112, 114, 116 may be configured to be positioned in relation to the subject 102 for accurately acquiring the ECG signal. The electrodes 112, 114, 116 may be identical electrodes, which may each be configured to be positioned anywhere at the skin of the subject 102, such that a choice of placement may be freely made and the electrodes 112, 114, 116 may be flexibly arranged for acquiring the ECG signal. For instance, the electrodes 112, 114, 116 may be provided with an adhesive surface for attaching the electrodes 112, 114, 116 to the skin of the subject 102. According to an embodiment, the electrodes 112, 114, 116 may be configured to be arranged on a torso of the subject 102, as illustrated in FIG. 1. According to another embodiment, the electrodes 112, 114, 116 may be configured to be arranged around a body part, such as being arranged around a wrist or an ankle of the subject 102.

According to yet another embodiment, the electrodes 112, 114, 116 may be arranged on a common carrier, such as a common patch or a garment which may be configured to be worn at or around the torso of the subject 102 for correctly positioning the electrodes 112, 114, 116 in relation to the subject 102 for acquiring the ECG signal.

The ECG sensor 110 may be configured to acquire a 1-lead ECG using two or three electrodes 112, 114, 116. However, the ECG sensor 110 may alternatively be configured to acquire an ECG signal having 1-12 leads. The ECG sensor 110 may comprise a plurality of electrodes 112, 114, 116, such as up to ten electrodes.

The system 100 may further comprise an artery signal sensor 120. The artery signal sensor 120 may be configured to acquire an artery signal representative of pressure pulse wave propagation at a location in an artery of the subject 102.

The artery signal sensor 120 may be configured to be arranged in relation to the location in the artery of the subject 102 for acquiring the signal. For instance, the artery signal sensor 120 may be configured to be arranged in contact with the skin of the subject 102 at the location of the artery, such as being arranged at a neck of the subject 102 for acquiring an artery signal from the carotid artery.

The artery signal sensor 120 may acquire the artery signal by passive sensing, such as acquiring vibrations caused by pressure pulse wave propagation in the artery, or by active sensing, such as transmitting a signal to the artery and detecting a response to the transmitted signal for detecting pressure pulse wave propagation. Thus, the artery signal sensor 120 may comprise a transmitter for transmitting a signal to the artery and a receiver for receiving a signal from the artery. A single component may be used for both transmitting and receiving signals.

According to an embodiment, the artery signal sensor 120 may comprise a carrier, which may be configured to adhere to the skin of the subject 102, such as in the form of a patch, or which may be configured to be arranged in relation to a body part, such as around the neck, the torso or a wrist.

According to an embodiment, the artery signal sensor 120 may comprise an ultrasound sensor. Thus, the artery signal sensor 120 may be configured to transmit an ultrasound signal towards the artery and detect a response. According to an embodiment, the artery signal sensor 120 may comprise a plurality of micromachined ultrasonic transducers (MUT), such as capacitive cMUTs or piezoelectric pMUTs. A plurality of MUTs may be used for generating a combined electric signal based on receiving ultrasound signals in the plurality of MUTs. Using MUTs may facilitate the artery signal sensor being compact and possible to be arranged on a small carrier.

The ultrasound sensor may be configured to detect variations in diameter of the artery caused by a pressure pulse wave propagating through the artery such that a distension waveform may be detected.

According to another embodiment, the artery signal sensor 120 may comprise a photoplethysmogram sensor, comprising a light source for transmitting a light signal towards the artery and a light detector for detecting light transmitted or reflected by the artery for acquiring a signal representing pressure pulse wave propagation in the artery.

According to another embodiment, the artery signal sensor 120 may comprise an optical coherence tomography sensor, comprising a light source for transmitting a low-coherence light signal towards the artery, a light detector for detecting light reflected by the artery while suppressing diffusely scattered light.

According to another embodiment, the artery signal sensor 120 may comprise a piezoelectric tonometer, which may be configured to be in mechanical contact with the artery for detecting variations in pressure in the artery.

According to another embodiment, the artery signal sensor 120 may comprise a bioimpedance sensor, which may be configured to provide a current through the body of the subject 102 between two electrodes in contact with the skin and to detect an induced voltage between the same or two other electrodes, such that a change in impedance caused by pressure pulse wave propagation in the artery may be detected.

According to another embodiment, the artery signal sensor 120 may comprise a radio frequency sensor, which may be configured to transmit a radio frequency signal towards the artery and to detect a radio frequency signal reflected from the artery. The radio frequency sensor may not even need to be arranged in direct contact with the subject 102 for detecting the artery signal.

The system 100 may further comprise a processing unit 130, which may be configured to receive the ECG signal and the artery signal. The processing unit 130 may further be configured to process the ECG signal and the artery signal in order to determine a pulse wave velocity (PVW) of the subject 102, as will be further described below.

The processing unit 130 may be arranged in a common housing with the ECG sensor 110 or the artery sensor 120. However, according to an alternative, the processing unit 130 may be arranged separately from the ECG sensor 110 and the artery sensor 120 and may be arranged to communicate with the ECG sensor 110 and the artery sensor 120 through wired or wireless communication for receiving the ECG signal and the artery signal, respectively.

The processing unit 130 may for instance be arranged in a wearable device enabling the processing unit 130 to be worn by the subject 102 such that the subject 102 may freely move while measurements are performed and the PWV is determined. According to an alternative, the processing unit 130 may be arranged in a server "in the cloud" and the ECG sensor 110 and the artery signal sensor 120 may be configured to communicate with the processing unit 130 through the Internet.

The processing unit 130 may be a central processing unit (CPU), which may execute the instructions of one or more computer programs in order to process the ECG signal and the artery signal. The processing unit 130 may also control functionality of the ECG sensor 110 and the artery signal sensor 120 such as for triggering start of acquisition of the ECG signal and the artery signal.

The processor 130 may alternatively be implemented as firmware arranged e.g. in an embedded system, or as a specifically designed processing unit, such as an Application-Specific Integrated Circuit (ASIC) or a Field-Programmable Gate Array (FPGA), which may be configured to implement functionality for processing the ECG signal and the artery signal.

The system 100 may further comprise additional artery signal sensor(s) 140. An additional artery signal sensor 140 may be configured to acquire a second artery signal in relation to a second location of an artery different from the first location at which the artery signal sensor 120 acquires a first artery signal.

The additional artery signal sensor 140 may for instance be configured to acquire a second artery signal in relation to a peripheral artery, such as an artery at a wrist of the subject 102.

Figure 2:
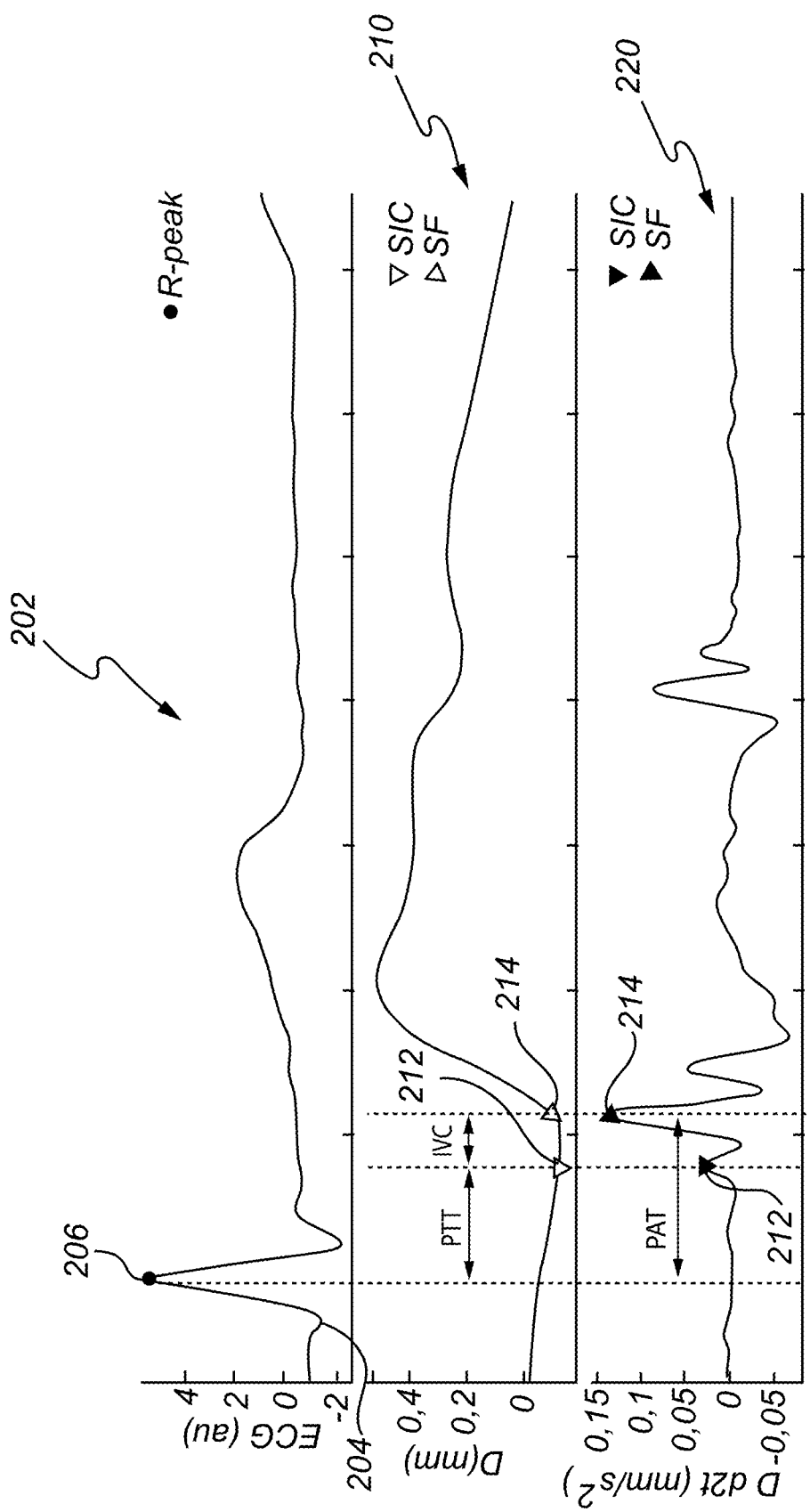
FIG. 2 is a schematic view of an ECG signal, an artery signal and a second derivative of the artery signal, illustrating processing of the signals for determining a vascular transit time.

Referring now to FIG. 2, processing of the ECG signal and the artery signal for estimating a PWV of the subject will be described in further detail.

In FIG. 2, the top graph shows the ECG signal 202, the middle graph shows the artery signal 210 in the form of a distension waveform, and the bottom graph shows a second derivative 220 of the artery signal 210.

In the ECG signal 202, a feature may be extracted which may be related to the onset of isovolumetric contraction (IVC) of the subject's heart. A cardiac cycle comprises a pre-ejection period (PEP) starting at the Q-wave 204 in the ECG signal 202. The PEP comprises an electromechanical delay (EMD) followed by the IVC.

Although the onset of IVC may not be directly detected in the ECG signal 202, the feature extracted from the ECG signal may be related in a known or determinable manner to the onset of IVC. Thus, by extracting a feature from the ECG signal, a fiducial point in time is determined which may allow a corresponding onset of IVC in the ECG signal to be determined using a known offset to the extracted feature.

According to an embodiment, an R-peak 206 may be detected in the ECG signal 202. The R-peak 206 may be suitably used as it may be easily detected in the ECG signal 202.

The EMD can be assumed to be constant at 40 ms, and it may further be assumed that half of the EMD elapse between the Q-wave 204 and the R-peak 206, such that the R-peak 206 precedes the onset of the IVC by 20 ms for determining the onset of IVC based on the detected R-peak 206.

A pre-systolic pressure pulse arrival point in time 212 corresponding to onset or start of the isovolumetric contraction (SIC) may be determined in the artery signal 210. The pre-systolic pressure pulse arrival point in time 212 is particularly visible in the second derivative 220 of the artery signal 210 and may hence be determined as a local maximum in the second derivative 220 of the artery signal 210.

In FIG. 2, it is further illustrated a pulse arrival time (PAT) corresponding to a time from onset of the IVC to an arrival time 214 of the pressure pulse at the artery, a systolic foot of the distension waveform ($SF_D$).

The PAT has been used for determining PWV and/or blood pressure of subjects, but such determinations do not take into account inter-subject variations of the IVC duration. According to the present inventive concept, a vascular or pulse transit time (PTT) is used instead, wherein the time period between the onset of the IVC of the subject's heart to a reflection or manifestation of the onset of the IVC at the location of the artery is determined.

Thus, in line with FIG. 2, the following definitions may be made.

The PAT may be defined as:

$$\text{PAT} = (t_{SF_D} - t_{R\text{-}peak}) - 0.5\ \text{EMD} \quad (\text{Eq. 1})$$

The PTT may be defined as:

$$\text{PTT} = \text{PAT} - \text{IVC} - \text{EMD} \quad (\text{Eq. 2})$$

The implicit determination of the IVC duration may be defined as:

$$\text{IVC} = (t_{SF_D} - t_{SIC}) \quad (\text{Eq. 3})$$

Based on Eq. 1 and Eq. 3, PTT in Eq. 2 may be rewritten as:

$$\begin{aligned} PTT &= (t_{SF_D} - t_{R\text{-}peak}) - (t_{SF_D} - t_{SIC}) - 0.5\ EMD \\ &= (t_{SIC} - t_{R\text{-}peak}) - 0.5\ EMD \end{aligned} \quad (\text{Eq. 4})$$

Finally, the PWV based on the PTT may be defined as:

$$PWV = \frac{L}{PTT} \quad (\text{Eq. 5})$$

wherein L is a distance from the aortic valve to the location in the artery. For instance, if the artery signal 210 is acquired from the carotid artery, a distance $L_{SN\text{-}CCA}$ from the sternal notch to common carotid artery on the neck may be used. The distance may be determined by measuring the distance outside the body of the subject 102.

The measured distance may not provide an exact measurement of an actual length of the distance along arteries from the aortic valve to the location at the artery. However, an error in the measured distance may be compensated for by a compensation factor. For instance, for the distance $L_{SN\text{-}CCA}$ a compensation factor of 2.5 may be used to account for underestimation of the actual arterial path length (~0.5 in ventral and ~2 in cranial direction). It should be realized that this compensation factor is variable and the appropriate compensation factor to be used may differ between different subjects. For instance, the compensation factor could be varied between 2.4-2.6.

As is evident from the above, the PWV may be determined directly based on determination of the fiducial point in time (R-peak) in the ECG signal 202, knowledge of offset of onset of the IVC from the fiducial point in time (0.5 EMD) and determination of the pre-systolic pressure pulse arrival point in time (SIC) in the artery signal 210 using only Eq. 4 and Eq. 5. However, it should also be realized that instead of directly using Eq. 4, the PTT may alternatively be determined by first determining PAT and IVC separately and then determining the PTT using Eq. 2. It should further be realized that the EMD duration may vary between subjects such that different values for EMD may be used for different subjects. For instance, the EMD duration may vary between 35-45 ms.

Since the R-peak 206 may be determined for each cardiac cycle in the ECG signal 202 and the pre-systolic pressure pulse arrival point in time 212 may also be determined for each cardiac cycle in the artery signal 210, it is possible to determine PWV for each cardiac cycle. Hence, variations in PWV may be determined per cardiac cycle, which provides a high temporal resolution for estimating the cardiovascular health of the subject 102.

The determined PWV may further be used for determining a corresponding blood pressure, such that an estimate of the blood pressure of the subject 102 may be determined. The blood pressure may also be determined for each cardiac cycle.

If additional artery signals are acquired using additional artery signal sensors 140, the PWV may be determined for each location from which an artery signal is acquired. The PWV may be determined using Eq. 4 and Eq. 5 for each location with corresponding distances L.

However, the IVC duration provides a common offset of the PAT in relation to the PTT for all artery signal sensors 120, 140. Hence, the IVC duration may be determined using Eq. 3 for one artery signal sensor 120, 140 only. Then, for the other artery signal sensors 120, 140, PAT may be determined from signal processing by determining $SF_D$ in the artery signal 210 and PTT may be determined as PTT=PAT−IVC, since IVC is known.

Further, a PWV between two artery signal sensors 120, 140 may be determined by comparing corresponding features in the artery signals 210 only. For instance, a systolic foot of the first distension waveform ($SF_{D,\ 1}$) of a first artery signal may be compared to a systolic foot of the second distension waveform ($SF_{D,\ 2}$) and PTT=$SF_{D,\ 1} - SF_{D,\ 2}$ may be used in combination with a distance L representing a difference in arterial path length of the locations for determining the PWV between the artery signal sensors 120, 140.

Figure 3:
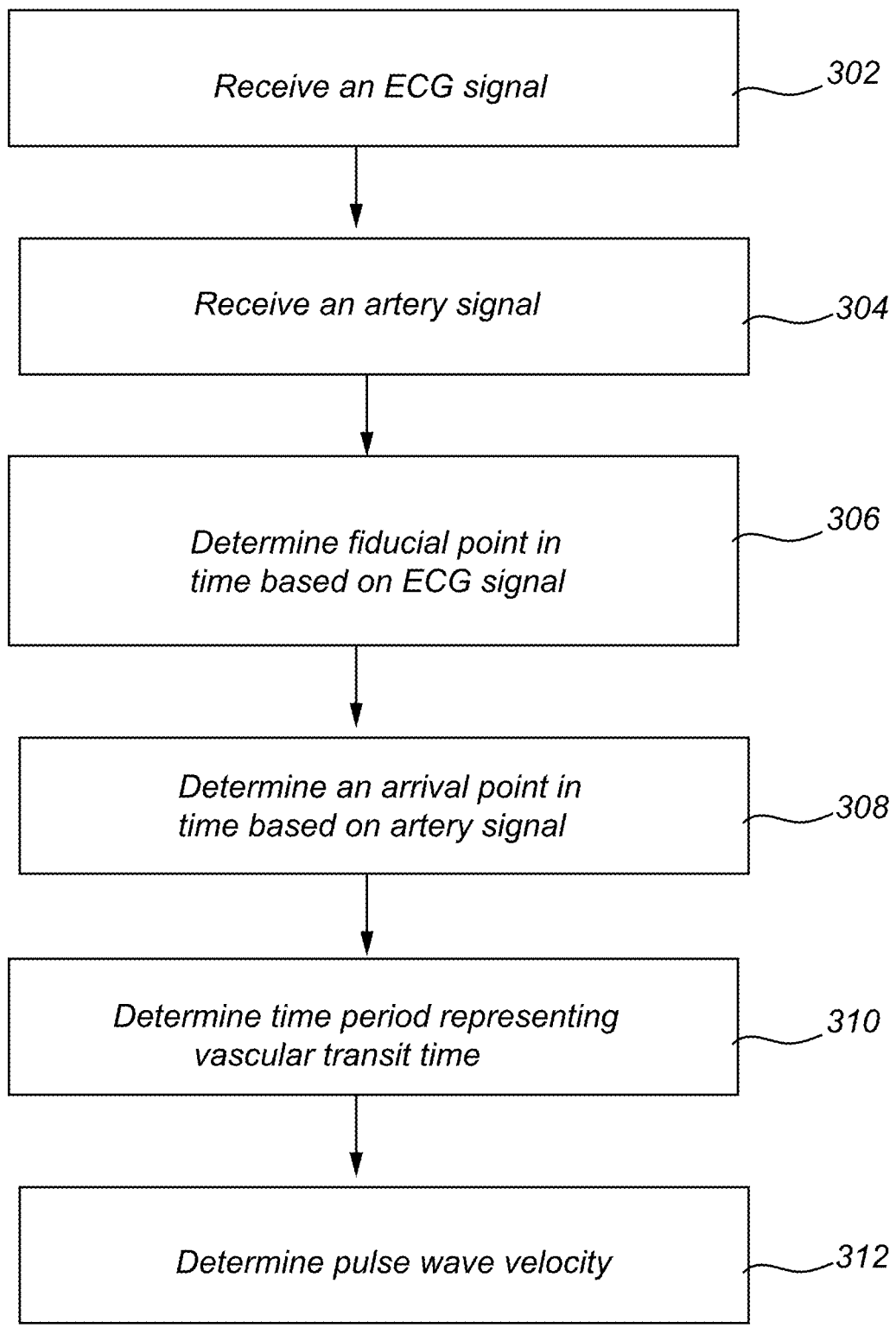
FIG. 3 is a flow chart of a method according to an embodiment.

Referring now to FIG. 3, a method for estimating the cardiovascular health in accordance with the discussion above will be briefly summarized. As mentioned above, the method may be implemented by a computer program product comprising computer-readable instructions being executed on a processing unit, or by processing performed by a specifically designed processing unit.

The method comprises receiving 302 an ECG signal of the subject.

The method further comprises receiving 304 an artery signal representative of pressure pulse wave propagation at a location in an artery of the subject.

The method further comprises processing the ECG signal to determine 306 a fiducial point in time based on the ECG signal. The fiducial point in time is determined to provide an indication of onset of isovolumetric contraction of the subject's heart.

The method further comprises processing the artery signal to determine 308 a pre-systolic pressure pulse arrival point in time based on the artery signal. The pre-systolic pressure pulse arrival point in time is determined to correspond to the onset of the isovolumetric contraction of the subject's heart being reflected in the artery signal.

The method further comprises determining 310 a time period representing a vascular transit time between the onset of the isovolumetric contraction of the subject's heart and reflection of the onset of the isovolumetric contraction of the subject's heart in the artery signal based on the fiducial point in time and the pre-systolic pressure pulse arrival point in time, said time period representing a vascular transit time.

The method further comprises determining 312 a pulse wave velocity of the subject based on a physical distance between an aortic valve and the location in the artery and on the vascular transit time.

The method for determining PWV has been tested in order to verify that the method is able to accurately determine PWV.

Data was acquired from 10 human subjects (7 male, 3 female) of age 38±10 years with a mean arterial pressure (MAP=⅓ Systolic Blood Pressure (SBP)+⅔ Diastolic Blood Pressure (DBP)) 91±10 mmHg.

An artery signal was acquired by carotid artery B-mode ultrasound recording. ECG was recorded in lead II configuration and peripheral photoplethysmogram (PPG) waveforms were recorded at 660 nm wavelength on the left index finger. Continuous blood pressure (BP) was recorded applying the volume-clamp technique on the left middle finger accompanied by intermittent oscillometric cuff BP.

Data was collected in three equally repeated measurement sessions, spread over three weeks, to account for physiological intra-, and inter-subject variability as well as technical measurement bias, e.g. due to sensor reattachment and probe repositioning. Before the first session demographics (gender, age, height, weight) and anthropometrics were measured to estimate the central and peripheral arterial path lengths, namely the sternal notch to common carotid artery halfway along the neck length ($L_{SN-CCA}$) and sternal notch to left index finger ($L_{SN-LIF}$), respectively. All data was recorded at constant room temperature (22° C.), in supine position to eliminate the hydrostatic BP component, and with an initial resting phase of 10 minutes. Each session, in turn, comprised three interventions. First, 2 minutes in resting conditions were recorded for best inter-subject comparability. Second, the subject was asked to perform 2 minutes of paced breathing to induce cyclic BP variation at 7.5 cycles per minute, guided by an acoustic reference signal. Third, to induce a short-term gradual BP increase, the subject was asked to perform a hand grip dynamometer exercise with the sensor free hand for 1 minute at maximal voluntary contraction, followed by 1 minute of recovery. Continuous BP was obtained throughout the interventions for detailed investigation of relative changes and intermittent cuff BP as gold standard measure pre-, and post relaxation and hand grip.

The following interval features were computed from intra-beat fiducial timestamps; the PPG-based peripheral PAT $$pPAT = (t_{SF_{PPG}} - t_{R-peak}) - 0.5 EMD \quad \text{(Eq. 6)}$$

with corresponding pPAT-based PWV $$pPWV_{PAT} = \frac{L_{SN-LIF}}{pPAT} \quad \text{(Eq. 7)}$$

the distension-based central PAT $$cPAT = (t_{SF_D} - t_{R-peak}) - 0.5 EMD \quad \text{(Eq. 8)}$$

with corresponding cPAT-based PWV $$cPWV_{PAT} = \frac{2.5\ L_{SN-CCA}}{cPAT} \quad \text{(Eq. 9)}$$

and the distension-based central PTT $$cPTT = (t_{SIC} - t_{R-peak}) - 0.5\ EMD \quad \text{(Eq.10)}$$

with implicit IVC definition $$IVC = t_{SF_D} - t_{SIC} \quad \text{(Eq. 11)}$$

and corresponding cPTT-based PWV $$cPWV_{PTT} = \frac{2.5\ L_{SN-CCA}}{cPTT} \quad \text{(Eq. 12)}$$

The electromechanical delay EMD was assumed constant at 40 ms and corrected by a factor 0.5 as it is partially comprised in cPTT with a constant ECG Q-R interval of approximately 20 ms.

Figure 4:
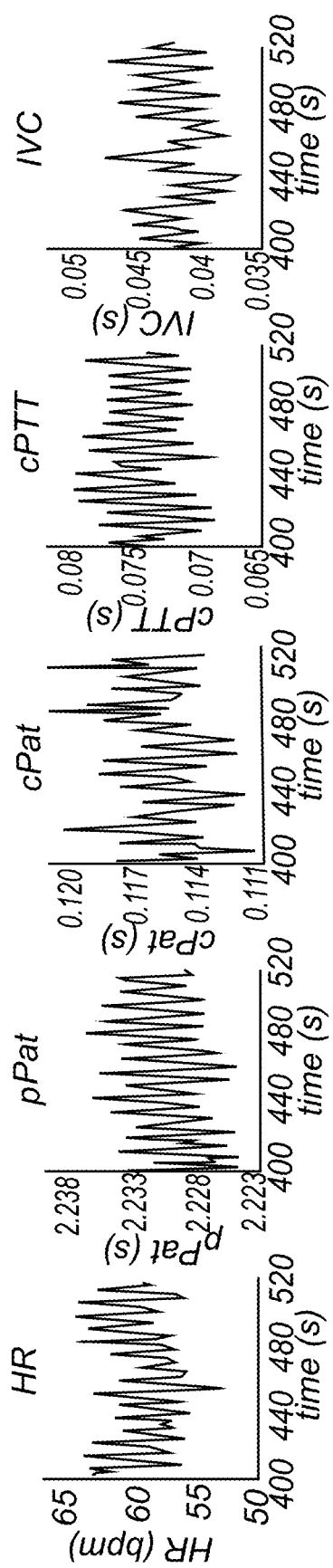
FIG. 4 shows an example from an experiment of intra-subject recording throughout paced breathing intervention, wherein graphs illustrate recorded time-series signals and correlations of determined measures to systolic blood pressure (SBP).
Figure 4:
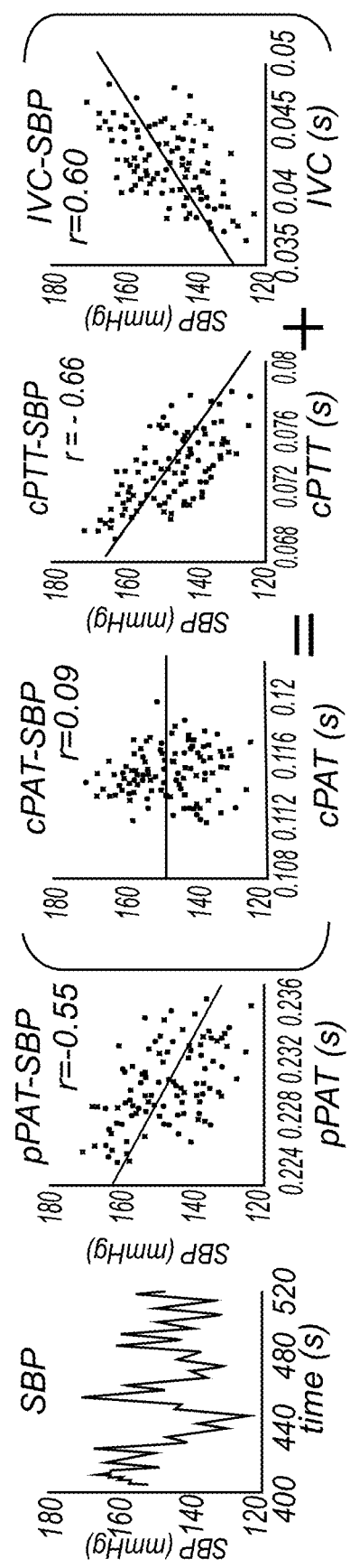

FIG. 4 gives a typical intra-subject example of the paced breathing intervention with SBP in response to a subset of features, all shown as beat-to-beat timeseries and with corresponding scatterplots at the intersections. Timeseries signals are shown in top row and leftmost column of FIG. 4. Note that cPAT and cPTT are displayed without the subtracted 0.5 EMD.

In FIG. 4, it is evident that the expectedly negative correlation (r being used to represent a coefficient of correlation) between PAT and SBP is stronger for the peripheral (pPAT, r=−0.55) than the central path (cPAT, r=0.09). The relatively weak cPAT correlation can be explained by the expectedly positive relation between IVC and SBP (r=0.6), masking the strong correlation between SBP and the central PTT (cPTT, r=−0.66). This phenomenon is further driven by the relatively high IVC contribution to cPAT (43/115 ms) as compared to pPAT (43/230 ms), being approximately doubled (19% vs. 37%) in this example.

Overall, fiducial detection and feature extraction showed a good reproducibility. After qualification, 82% of the data was preserved, i.e. 74 of 90 and 98 of 120 datapoints corresponding to continuous and intermittent BP, respectively. Disqualified data consisted of one subject systematically exhibiting a high degree of lateral carotid artery displacement, making SIC unidentifiable, and random datapoints among the remainders, respectively accounting for 10% and 8% of the discarded data.

For the statistical analysis, data corresponding to the continuous BP was compressed to median feature values per subject, session and intervention. Only the recovery after hand grip was excluded to avoid hysteresis of the vascular compliance. Similarly, data corresponding to the intermittent cuff BP, i.e. the 15 first and last qualified cardiac cycles from the relaxation and hand grip intervention, were compressed to median values.

The compressed feature data entered a set of least squares linear regression analyses with SBP, DBP, pulse pressure (PP), heart rate (HR) and Bramwell-Hill pulse wave velocity ($PWV_{BH}$) as dependent variables x, and various PAT, PTT, PWV and Bramwell-Hill pressure change ($dP_{BH}$) quantities as independent variables y, respectively of the form $y=\beta x+\alpha$. Main outcomes were the coefficients of correlation (r) and determination ($R^2$), the root mean squared error (RMSE), the F-statistic for correlation significance as well as residual errors for BP standard metrics. That is, from the residual errors the mean ($\mu$), standard deviation ($\sigma$) and mean absolute deviation (MAD, i.e. mean of absolute errors) were computed, which serve as error metrics in the common IEEE and Association for the Advancement of Medical Instrumentation (AAMI) BP validation standards. The IEEE standard is graded and allows for a MAD 5 to receive grade A while MAD 7 receives grade D, and the AAMI standard is of binary outcome and allows for $\mu \leq \pm 5$ mmHg and $\sigma \leq 8$ mmHg. Ultimately, to test the differences of the error metrics between predictors, a paired-sample t-test for mean equality was conducted for the IEEE MAD ($MAD_{IEEE}$) and a two sample F-test for variance equality for the AAMI $\sigma$ ($\sigma_{AAMI}$), while the AAMI $\mu$ equals 0 by definition in linear regression.

In addition, a sensitivity analysis was conducted to demonstrate the impact of arterial path length inaccuracies on PWV computation. For this purpose, uniform white noise of 1 cm and 5 cm was added around the manually assessed distances LSN-CCA (9.5±1.5 cm) and LSN-LIF (87.4±7.6 cm), respectively simulating an approximate 10% and 5% variability in path length. Noise was added simultaneously to all subjects in 100 variations, yet randomly per subject, resulting in 100 iterations of the regression analyses.

Figure 5:
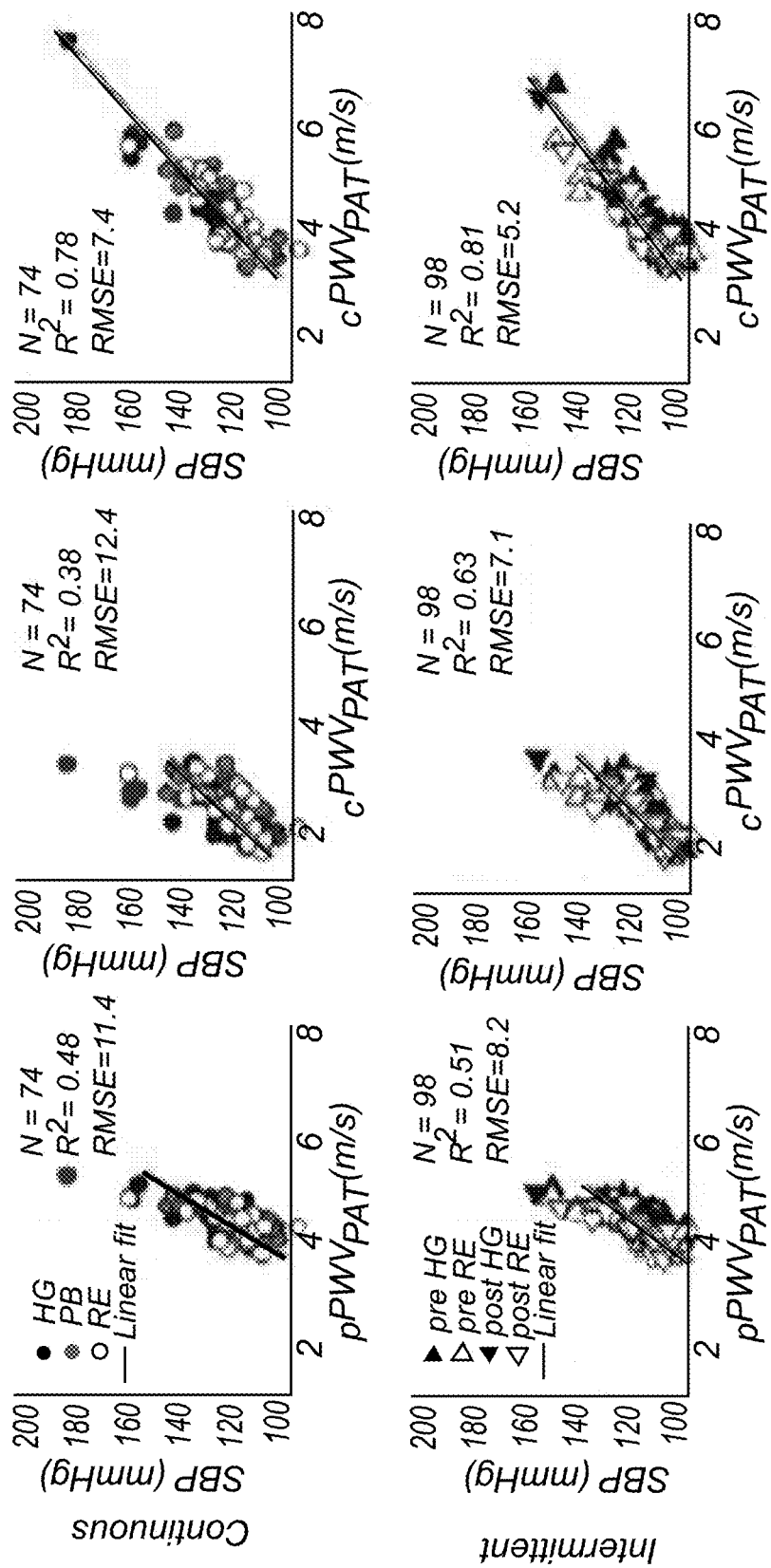
FIG. 5 shows an excerpt from an experiment of the linear regression analysis with continuous and intermittent SBP responses to the pulse wave velocity (PV V) predictors.

FIG. 5 shows an excerpt of the linear regression analysis with continuous and intermittent SBP responses to the PWV predictors. In FIG. 5, the following abbreviations and denotations are used: N: number of samples; HG: hand grip; PB: paced breathing; RE: relaxation.

For the combined intra-, and inter-subject data, the central PTT-based PWV compared to peripheral PAT-based PWV ($cPWV_{PTT}$ vs. $pPWV_{PAT}$) yielded a ~30% higher predictive utility for SBP (continuous: $R^2=0.78$ vs. 0.48; intermittent: $R^2=0.81$ vs. 0.51). However, the predictive utility of central PAT-based PWV for SBP decreased compared to its peripheral equivalent for continuous responses ($pPWV_{PAT} R^2=0.48$ vs. $cPWV_{PAT} R^2=0.38$) but increased for intermittent responses ($pPWV_{PAT} R^2=0.51$ vs. $cPWV_{PAT} R^2=0.63$). An overall congruence between the continuous and intermittent data was observed with similar correlations across all types of predictors (PAT, PTT, PWV, $dP_{BH}$) and responses (SBP, DBP, PP, HR, $PWV_{BH}$), irrespective of the paced breathing intervention as comprised by the continuous data only. Therefore, the following results focus on intermittent BP as gold standard reference only.

Figure 6:
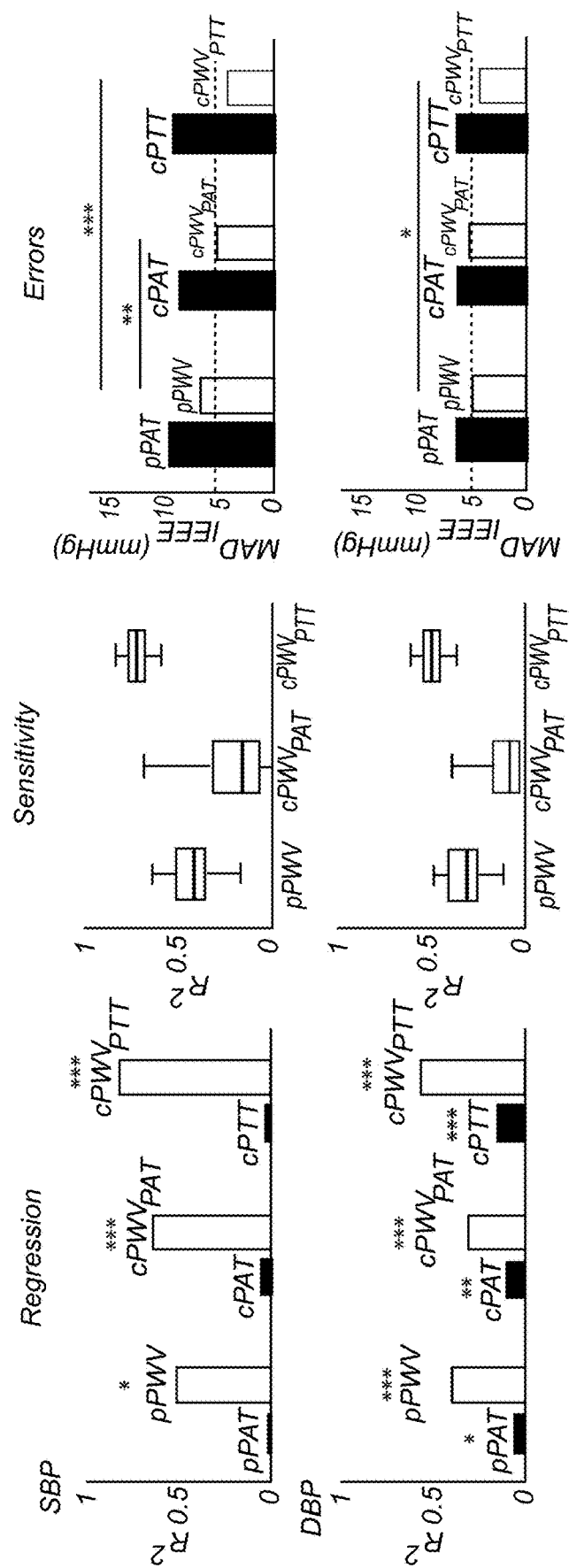
FIG. 6 shows a regression bar chart (left), a sensitivity boxplot (center) and mean absolute deviation from IEEE standard ($MAD_{IEEE}$) error bar chart (right), respectively for intermittent systolic blood pressure (top row) and diastolic blood pressure (bottom row).

FIG. 6 shows a regression bar chart (left), a sensitivity boxplot (center) and $MAD_{IEEE}$ error bar chart (right), respectively for intermittent systolic blood pressure (top row) and diastolic blood pressure (bottom row). * denotes a P-value of statistical significance, $P<0.05$;  denotes a P-value of statistical significance, $P<0.01$, and * denotes a P-value of statistical significance, $P<0.001$. A paired-sample t-test is used for the $MAD_{IEEE}$.

FIG. 6 highlights the results of the regression, sensitivity and error analyses. Here the strongest predictive utility for SBP ($R^2=0.81$) and DBP ($R^2=0.55$) was found for $cPWV_{PTT}$, excelling compared to any other PWV, PAT or PTT interval predictor, while $cPWV_{PAT}$ is the strongest predictor for PP ($R^2=0.46$). Furthermore, for SBP and DBP, the beta correlation coefficients indicate a substantial nonlinearity in the relation with PWV.

For DBP, significance of the interval predictors increased gradually with a purer, more central PTT (pPAT: $P<0.05$, cPAT: $P<0.01$, cPTT: $P<0.001$). Relating to this, an average IVO contribution is 37 ms (i.e. the mean difference in range between cPAT and cPTT), accounting for 16.7% of pPAT and 32.4% of cPAT.

The center boxplots in FIG. 6 reveal the sensitivity to the simulated path length variability, for which $cPWV_{PTT}$ shows an outstanding robustness, i.e. the highest, narrowest and least skewed $R^2$ distribution for both SBP and DBP.

Similar outcomes manifested in the error metrics, where the right plots in FIG. 6 show that only $cPWV_{PTT}$ undercuts the $MAD_{IEEE}$ 5 mmHg threshold, in fact significantly lower than $pPWV_{PAT}$ for all SBP ($P<0.001$), DBP ($P<0.05$) and PP ($P<0.05$, not in graph). For PP, only $cPWV_{PAT}$ showed an even higher significance ($P<0.01$) and lower error than $cPWV_{PTT}$, reflecting the regression results findings. Moreover, all cPWV predictors undercut the $\sigma_{AAMI}$ threshold of 8 mmHg, but only the variances of $cPWV_{PTT}$ for SBP ($P<0.001$) and $cPWV_{PAT}$ for PP ($P<0.05$) were significantly lower than $pPWV_{PAT}$.

HR did not significantly correlate with any cPWV, but showed significant correlations with $pPWV_{PAT}$ and all intervals, particularly pPAT ($R^2=0.51$, $P<0.001$).

For the Bramwell-Hill PWV the significance of interval predictors increased gradually with a more central and purer PTT, similar to DBP. The predictive utility for $PWV_{BH}$ almost doubled from $pPWV_{PAT}$ ($R^2=0.26$) to $cPWV_{PTT}$ ($R^2=0.51$). However, it shall be noted that $cPWV_{PTT}$ systematically underestimated $PWV_{BH}$ (difference in mean value, $\Delta\mu$: 2.9 m/s; difference in standard deviation $\Delta\sigma$: 0.8 m/s).

For the estimation of PP from pressure change $dP_{BH}$ based on the inverse Bramwell-Hill equation, correlations increased significantly when computing $dP_{BH}$ from $cPWV_{PTT}$ as compared to pPWV ($R^2$: 0.35, $P<0.001$ compared to $R^2$: 0.04, $P<0.05$). Still, the predictive utility of $dP_{BH}$ from $cPWV_{PTT}$ for PP remained below that of $cPWV_{PAT}$.

In summary, correlations with gold standard BP and $PWV_{BH}$ improved significantly from the combination of 1) measuring PAT along a central arterial path, 2) segmenting PAT into IVO and PTT, and 3) converting PTT intervals into PWV using estimated path lengths. The latter step is highly relevant to render PWV into a physiologically valid range for inter-subject comparability. For the sake of completeness, PWV was also estimated from (fractions of) body height, but correlations were found to lie between those from PAT or PTT intervals and PWV from specific distances, and insufficient to achieve the IEEE or AAMI error margins.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For instance, the pre-systolic pressure pulse arrival point in time need not be determined based on the second derivative 220 of the artery signal 210. Alternatively, the pre-systolic pressure pulse arrival point in time may be determined based on analysis of the artery signal, a first derivative of the artery signal, a third derivative of the artery signal, or fitting a Gaussian curve to the second derivative of the artery signal.

The invention claimed is:

1. A method for estimating a measure of cardiovascular health of a subject, said method comprising:
receiving an electrocardiogram, ECG, signal of the subject;
receiving an artery signal representative of pressure pulse wave propagation at a location in an artery of the subject, wherein the artery signal is received from a sensor at a single location of the artery;
determining a fiducial point in time based on the ECG signal, said fiducial point in time providing an indication of onset of isovolumetric contraction of the subject's heart;
determining a pre-systolic pressure pulse arrival point in time based on the artery signal, wherein the pre-systolic pressure pulse arrival point in time is determined to correspond to the onset of the isovolumetric contraction of the subject's heart being reflected in the artery signal,
determining a time period between the onset of the isovolumetric contraction of the subject's heart and reflection of the onset of the isovolumetric contraction of the subject's heart in the artery signal based on the fiducial point in time and the pre-systolic pressure pulse arrival point in time, said time period representing a vascular transit time; and
determining a pulse wave velocity of the subject based on a physical distance between an aortic valve and the location in the artery and on the vascular transit time,
wherein determining the fiducial point in time comprises determining an R peak in the ECG signal,
wherein the onset of the isovolumetric contraction of the subject's heart is offset from the fiducial point in time by a half of an electromechanical delay period, wherein the offset is less than 40 ms.

2. The method according to claim 1, wherein determining the pre-systolic pressure pulse arrival point in time comprises determining a second derivative of the artery signal and determining a local maximum in the second derivative.

3. The method according to claim 1, wherein the artery signal is received from an ultrasound sensor.

4. The method according to claim 3, wherein the received artery signal comprises an ultrasound-based distension waveform.

5. The method according to claim 1, wherein the artery signal is received from an optical sensor, a piezoelectric tonometer, a bioimpedance sensor or a radio frequency sensor.

6. The method according to claim 1, wherein the received artery signal is representative of pressure pulse wave propagation at a location in a carotid artery.

7. The method according to claim 1, further comprising estimating blood pressure of the subject based on the determined pulse wave velocity.

8. The method according to claim 1, wherein determining the fiducial point in time comprises determining a Q point in the ECG signal.

9. The method according to claim 1, wherein said artery signal is a first artery signal representative of pressure pulse wave propagation at a first location in a first artery of the subject, said pre-systolic pressure pulse arrival point in time is a first pre-systolic pressure pulse arrival point in time, said time period is a first time period, said vascular transit time is a first vascular transit time, and said pulse wave velocity is a first pulse wave velocity, said method further comprising:
receiving a second artery signal representative of pressure pulse wave propagation at a second location in the first artery of the subject or in a second artery of the subject;
determining a second pre-systolic pressure pulse arrival point in time based on the second artery signal, wherein the second pre-systolic pressure pulse arrival point in time is determined to correspond to the onset of the isovolumetric contraction of the subject's heart being reflected in the second artery signal,
determining a second time period between the onset of the isovolumetric contraction of the subject's heart and reflection of the onset of the isovolumetric contraction of the subject's heart in the second artery signal based on the fiducial point in time and the second pre-systolic pressure pulse arrival point in time, said second time period representing a second vascular transit time; and
determining a second pulse wave velocity of the subject based on a physical distance between the aortic valve and the second location and on the second vascular transit time.

10. A computer program product comprising computer-readable instructions stored on a non-transitory computer-readable storage medium such that when executed on a processing unit the computer-readable instructions will cause the processing unit to perform the method according to claim 1.

11. A system for estimating a measure of cardiovascular health of a subject, said system comprising:
an electrocardiogram (ECG) sensor configured to acquire an ECG signal of the subject;
an artery signal sensor configured to acquire an artery signal representative of pressure pulse wave propagation at a single location in an artery of the subject; and
a processor configured to:
receive the ECG signal and the artery signal;
determine a fiducial point in time based on the ECG signal, said fiducial point in time providing an indication of onset of isovolumetric contraction of the subject's heart;
determine a pre-systolic pressure pulse arrival point in time based on the artery signal, wherein the pre-systolic pressure pulse arrival point in time is determined to correspond to the onset of the isovolumetric contraction of the subject's heart being reflected in the artery signal,
determine a time period between the onset of the isovolumetric contraction of the subject's heart and reflection of the onset of the isovolumetric contraction of the subject's heart in the artery signal based on the fiducial point in time and the pre-systolic pressure pulse arrival point in time, said time period representing a vascular transit time; and
determine a pulse wave velocity of the subject based on a physical distance between an aortic valve and the location in the artery and on the vascular transit time,
wherein determining the fiducial point in time comprises determining an R peak in the ECG signal,
wherein the onset of the isovolumetric contraction of the subject's heart is offset from the fiducial point in time by a half of an electromechanical delay period, wherein the offset is less than 40 ms.

* * * * *